(12) United States Patent  
Leach et al.

(10) Patent No.: US 11,291,860 B2  
(45) Date of Patent: Apr. 5, 2022

(54) SHIM SYSTEM FOR A MAGNETIC RESONANCE HYBRID SCANNER

(71) Applicant: KONINKLIJKE PHILIPS N.V., Eindhoven (NL)

(72) Inventors: Jeffrey Edward Leach, Rexford, NY (US); Philip Alexander Jonas, Delmar, NY (US); Johannes Adrianus Overweg, Hamburg (DE); Viktor Mokhnatyuk, Castleton On Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 29 days.

(21) Appl. No.: 16/856,356

(22) Filed: Apr. 23, 2020

(65) Prior Publication Data

US 2020/0246636 A1    Aug. 6, 2020

Related U.S. Application Data

(62) Division of application No. 14/899,154, filed as application No. PCT/IB2014/062415 on Jun. 19, 2014, now Pat. No. 10,661,098.

(60) Provisional application No. 61/924,952, filed on Jan. 8, 2014, provisional application No. 61/837,805, filed on Jun. 21, 2013.

(51) Int. Cl.
*A61N 5/10* (2006.01)
*G01R 33/3873* (2006.01)
*G01R 33/48* (2006.01)
*G01R 33/3875* (2006.01)

(52) U.S. Cl.
CPC ......... *A61N 5/1039* (2013.01); *A61N 5/1077* (2013.01); *G01R 33/3873* (2013.01); *G01R 33/3875* (2013.01); *G01R 33/4808* (2013.01)

(58) Field of Classification Search
CPC ............... A61N 5/1039; A61N 5/1077; G01R 33/3873; G01R 33/3875; G01R 33/4808
See application file for complete search history.

(56) References Cited

U.S. PATENT DOCUMENTS

| | | |
|---|---|---|
| 5,418,462 A | 5/1995 | Breneman |
| 5,550,472 A | 8/1996 | Richard |
| 5,773,976 A | 6/1998 | Sakakura |

(Continued)

FOREIGN PATENT DOCUMENTS

| | | |
|---|---|---|
| EP | 0715181 A1 | 6/1996 |
| GB | 2484788 A | 4/2012 |

(Continued)

*Primary Examiner* — Dixomara Vargas
(74) *Attorney, Agent, or Firm* — Sherry Austin

(57) ABSTRACT

A magnetic resonance apparatus which may include: a body portion having a cavity with a first and second ends and at least one opening situated at one of the first and second ends. The cavity may define a longitudinal axis (LA) extending between the first and second ends. At least one main magnet may generate a main magnetic field having a substantially homogenous magnetic field within the cavity. A center shim (CS) which may be formed from a ring having opposed edges and which may extend along a length of the longitudinal axis of the cavity. One or more discrete shims (DSs) may be situated between the CS and at least one of the first and second ends.

20 Claims, 8 Drawing Sheets

(56) References Cited

U.S. PATENT DOCUMENTS

| | | |
|---|---|---|
| 6,255,928 B1 | 7/2001 | Van Oort |
| 6,335,670 B1 | 1/2002 | Kinanen |
| 7,295,012 B1 | 11/2007 | Lvovsky |
| 7,495,441 B2 | 2/2009 | Amor |
| 7,508,208 B2 | 3/2009 | Gleich |
| 7,646,274 B2 | 1/2010 | Rapoport |
| 7,884,605 B2 | 2/2011 | Tamura |
| 8,295,906 B2 * | 10/2012 | Saunders ............. A61N 5/1049 600/411 |
| 8,331,531 B2 * | 12/2012 | Fahrig ................. A61N 5/1049 378/65 |
| 8,362,778 B2 | 1/2013 | Slade |
| 8,798,715 B2 | 8/2014 | Rapoport |
| 8,896,308 B2 * | 11/2014 | Shvartsman ....... G01R 33/4808 324/318 |
| 8,981,779 B2 * | 3/2015 | Shvartsman ....... G01R 33/3806 324/320 |
| 9,269,484 B2 | 2/2016 | Ncginley |
| 9,297,874 B2 | 3/2016 | Rapoport |
| 9,664,763 B2 * | 5/2017 | Amthor ................. G01R 33/56 |
| 10,061,000 B2 * | 8/2018 | Longfield ......... G01R 33/4808 |
| 10,661,098 B2 * | 5/2020 | Leach ................. A61N 5/1077 |
| 2005/0085712 A1 | 4/2005 | Rapoport |
| 2006/0261812 A1 | 11/2006 | Ariyoshi |
| 2007/0030004 A1 | 2/2007 | Amor |
| 2007/0252598 A1 | 11/2007 | Lvovsky |
| 2009/0009171 A1 | 1/2009 | Tamura |
| 2009/0096453 A1 | 4/2009 | Barnes |
| 2010/0174172 A1 * | 7/2010 | Ein-Gal ............. G01R 33/4808 600/411 |
| 2010/0207630 A1 | 8/2010 | Barnes |
| 2010/0219833 A1 | 9/2010 | Ncginley |
| 2010/0237867 A1 | 9/2010 | Slade |
| 2011/0012593 A1 * | 1/2011 | Shvartsman ....... G01R 33/4808 324/307 |
| 2011/0121832 A1 * | 5/2011 | Shvartsman ....... G01R 33/3806 324/318 |
| 2011/0172518 A1 | 7/2011 | Rapoport |
| 2011/0260727 A1 * | 10/2011 | Punchard ........... G01R 33/3875 324/318 |
| 2013/0147476 A1 * | 6/2013 | Shvartsman ....... G01R 33/4808 324/309 |
| 2013/0225975 A1 * | 8/2013 | Harvey ................ A61N 5/1049 600/411 |
| 2014/0009152 A1 | 1/2014 | Sakakibara |
| 2014/0084926 A1 * | 3/2014 | Amthor ................. G01R 33/56 324/309 |
| 2014/0128719 A1 * | 5/2014 | Longfield .......... G01R 33/4808 600/411 |
| 2014/0135615 A1 * | 5/2014 | Kruip ................. G01R 33/4808 600/411 |
| 2014/0266206 A1 * | 9/2014 | Dempsey ............. G01R 33/481 324/322 |
| 2014/0266208 A1 * | 9/2014 | Dempsey ........... G01R 33/4808 324/322 |
| 2014/0275963 A1 * | 9/2014 | Shvartsman ......... A61N 5/1049 600/411 |
| 2015/0276897 A1 * | 10/2015 | Leussler ............ G01R 33/3614 324/322 |

FOREIGN PATENT DOCUMENTS

| | | |
|---|---|---|
| JP | 01254154 A | 10/1989 |
| JP | 0515506 A | 1/1993 |
| JP | H05220127 A | 8/1993 |
| JP | 2012154213 A | 8/2012 |
| WO | WO2004024235 A1 | 3/2004 |
| WO | WO2012164527 A1 | 12/2012 |

* cited by examiner

SHIM SYSTEM FOR A MAGNETIC RESONANCE HYBRID SCANNER

This application is a Divisional under 35 U.S.C. § 120 of U.S. patent application Ser. No. 14/899,154, filed Dec. 17, 2015, which claims priority to U.S. Provisional Patent Application No. 61/837,805, filed Jun. 21, 2013 and U.S. Provisional Patent Application No. 61/924,952, filed Jan. 8, 2014, the entire contents of which are incorporated herein by reference thereto.

The present system relates to a magnetic resonance imaging (MRI) system and, more particularly, to an MRI system with an improved shimming system suitable for magnetic resonance (MR)-guided radiation therapy, and a method of operation thereof.

Magnetic resonance scanners typically render images for diagnosing disease and contrasting healthy tissue from abnormal tissue. MR imaging can provide diagnostic spatial specificity in real time. Radiation therapy methods have been developed using a linear accelerator (LINAC) which can focus a radiation beam and preferentially destroy diseased tissue while sparing healthy tissue. However, when the radiation beam is focused on healthy tissue, it can damage the healthy tissue. Fortunately, the beam-focus technology of radiation therapy may be used with the diagnostic spatial specificity of real-time MR imaging so that the radiation beam can be accurately focused to treat diseased tissue while reducing or entirely preventing damage to healthy tissue. Systems which combine MR imaging and beam-focus technology are known as hybrid systems. One such hybrid system is commonly referred to as a magnetic resonance (MR) Linear Accelerator (LINAC) (MR-LINAC) system. MR-LINAC systems (also simply referred to as "MR-LINAC" for simplicity) combine real-time MR imaging with radiation therapy and can perform beam shaping in real-time, which can compensate for daily changes in anatomy (e.g., of a patient) and real-time body movement of the patient such as movement due to breathing, etc.

Unfortunately, when radiation therapy is combined with MR imaging, several difficulties may be encountered. The main magnetic field of an MRI system is typically produced by main magnets and is located in a main bore of the main magnets. It is preferable that the main magnetic field be homogenous within at least a scanning volume of the main bore so that proper MR image information (e.g., echo information) may be obtained and processed to construct images that have a desired image quality. However, the main magnetic field can be adversely influenced and become inhomogeneous by various factors such as manufacturing tolerances, imperfections in the main magnets, onsite shielding, stray fields, poor shimming, fields created by the MR-LINAC, etc. This inhomogeneity is undesirable as it can reduce image quality. Accordingly, shimming methods may be employed to correct for any inhomogeneity in the main magnetic field. However, conventional shimming methods using discrete pieces of steel would produce radiation shadows causing a non-uniform dose to be delivered to the patient if penetrated by a LINAC. Simply removing the discrete shim locations from the LINAC beam path would not allow the shim system to efficiently correct any field non-uniformity. An axially symmetric uniformity correction is required inside the region which is penetrated by the LINAC beam path.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed a magnetic resonance apparatus which may include: a body portion having a cavity with a first and second ends and at least one opening situated at one of the first and second ends, the cavity may define a longitudinal axis (LA) extending between the first and second ends. At least one main magnet may generate a main magnetic field having a substantially homogenous magnetic field within the cavity. A center shim (CS) may be formed from a ring having opposed edges and may extend along a length of the longitudinal axis of the cavity. One or more discrete shims (DSs) may be situated between the CS and at least one of the first and second ends.

In accordance with some embodiments, the CS may include a plurality of rings laminated upon each other. Each of the plurality of rings may have opposed ends situated apart from each other so as to define a gap. A filler may be situated within one or more of the gaps. Further, each of the gaps of each of the rings may be aligned with each other or rotationally offset from each other so as to be staggered. It is further envisioned that the DSs may include fine shims and coarse shims. Moreover, one or more rails may be provided, each of which may be configured to be coupled to corresponding ones of the shims such as the fine shims so as to form a shim cartridge. The rails may be further configured to be coupled to, and situated within, the body portion. In some embodiments, a locking mechanism may be provided to lock the shims in a desired position within the cavity of the body.

The apparatus may further include a radiation source that passes into an MRI system for purposes of preferentially destroying diseased tissue while sparing healthy tissue. For example, the apparatus may further include a linear accelerator (LINAC) which may generate and emit at least one radiation beam through an exclusion zone (Ez) within the cavity of the body. The Ez may have opposed ends and be situated within the cavity in a path of the at least one radiation beam emitted by the LINAC. The CS may be located at least in part within the Ez. It is further envisioned that at least one of the CS and the DSs may be configured to enforce uniformity of the main magnetic field within the cavity.

In accordance with yet other embodiments of the present system there is provided a device such as a magnetic resonance linear accelerator (MR-LINAC) apparatus, which may include: a body portion having a cavity having opposed ends and at least one opening situated at one of the opposed ends. The cavity may define a longitudinal axis (LA) extending between the first and second ends. At least one main magnet may generate a main magnetic field including a substantially homogenous magnetic field within the cavity. A linear accelerator (LINAC) may emit at least one radiation beam which passes through the cavity. The shim system may include an annular center shim (CS) with opposed edges and which substantially encircles and extends along the longitudinal axis (LA) of the body portion. The shim system may further include a plurality of discrete shims (DSs) situated between an edge of the opposed edges of the CS and an adjacent one of the opposed ends of the cavity. It is further envisioned that the CS may include a plurality of shim layers laminated upon each other. In accordance with some embodiments, the shim system may further include one or more rails each configured to be coupled to a plurality of the DSs.

In accordance with yet further embodiments of the present system there is provided a method of adjusting one or more fine shims of a magnetic-resonance (MR) system having a main magnet with a bore, an annular center shim located within the bore, the method performed by at least one controller of the MR system. The method may include acts of: controlling main magnets to output a nominal field within the bore of the main magnet; acquiring a magnetic field map of the magnetic field within the bore of the main magnet; and determining optimized locations for the shims on corresponding shim rails based upon an analysis of the magnetic field map. The method may further include an act of inserting at least one of the shim rails having the optimized rail locations for the fine shims into the bore of the main magnet. The method may also include an act of locking the at least one shim rails that is inserted in the bore of the main magnet using a locking mechanism. Further, the method may include an act of selecting a shim rail having the configuration of fine shims coupled to the shim rail in accordance with the determined optimized shim locations. In accordance with some embodiments, all shim rails of a body may be situated within the cavity regardless of locations of shims upon a corresponding rail or even if the corresponding rail includes no shims, as may be the case for some of the plurality of rails.

The present invention is explained in further detail in the following exemplary embodiments and with reference to the figures, where identical or similar elements are partly indicated by the same reference numerals, and the features of various exemplary embodiments being combinable. In the drawings.

Figure 1:
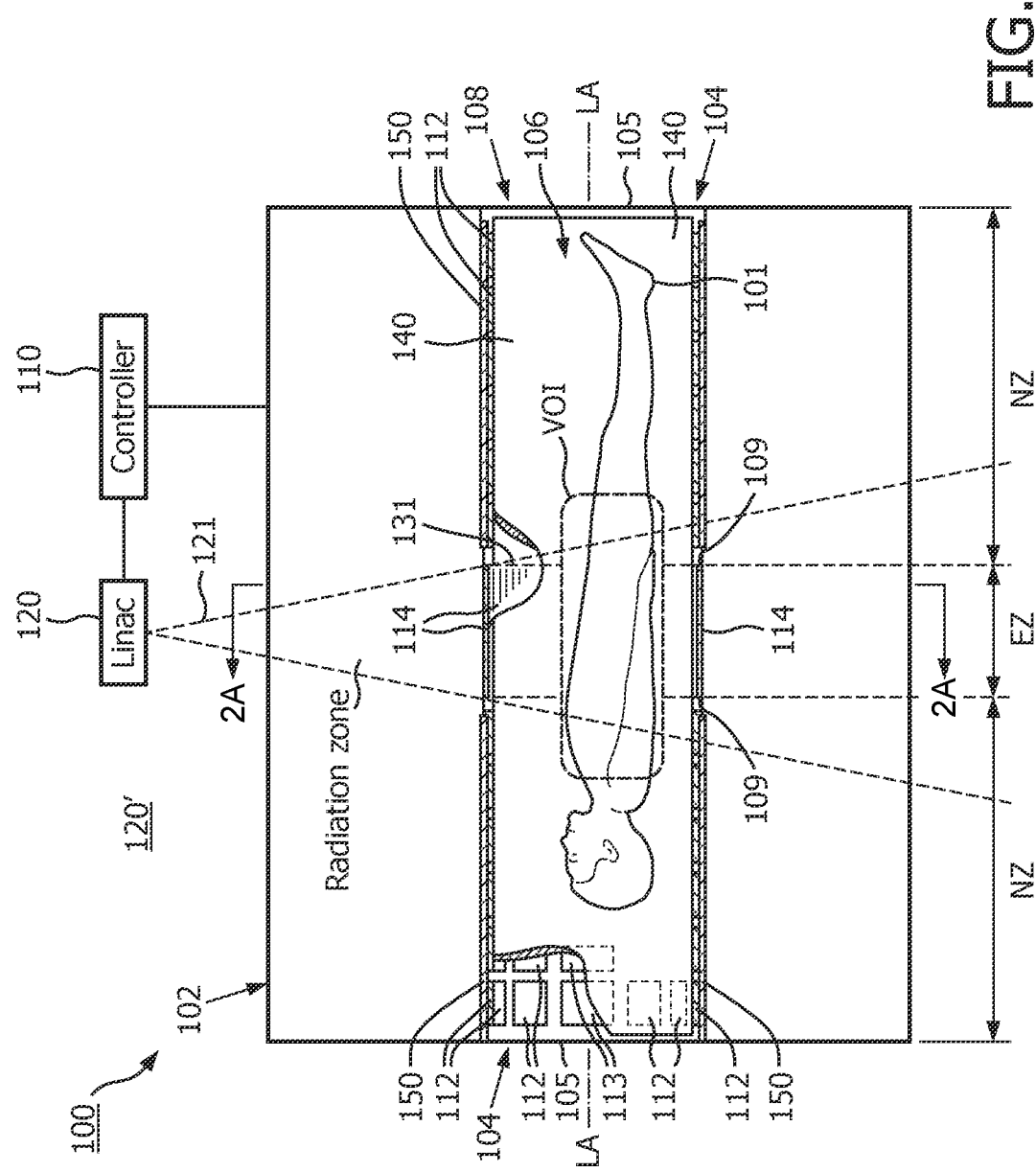
FIG. 1 shows a cutaway side view of a portion of system, such as an MR-LINAC system with a shimming system in accordance with embodiments of the present system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. Further, in some figures, cross-hatching may not be shown for the sake of clarity.

The present system is directed to radiation therapy devices and methods using a radiation source that passes into an MRI system for therapeutic purposes. For example, the present system may be suitably utilized for preferentially destroying diseased tissue of a subject while sparing healthy tissue. One such radiation therapy device for example, includes a linear accelerator (LINAC) which may generate and emit at least one radiation beam through an exclusion zone (Ez) within a cavity of a body of an MRI device. The Ez may have opposed ends and be situated within the cavity in a path of the at least one radiation beam emitted by the LINAC. In accordance with yet other embodiments of the present system there may be provided a magnetic resonance linear accelerator (MR-LINAC) apparatus as a radiation source.

For purposes of simplifying the following discussion, the embodiments of the present system will be discussed with regard to LINAC and MR-LINAC systems operating as the radiation source. It should however be expressly understood that embodiments of the present system may also be suitably applied with regard to other radiation sources that cooperate with the embodiments of the present system. As such, usage of the LINAC and MR-LINAC herein should be understood to include systems that utilize other radiation sources that may also be suitably applied.

Embodiments of the present system may employ shimming methods which may correct for inhomogeneity in the main magnetic fields of a main magnet by, for example, cancelling out gradients over a nuclear magnetic resonance (NMR) sample. Accordingly, a desired uniformity (e.g., homogeneity) of the main magnetic field that is essential for desired image quality may be obtained. Shimming methods in accordance with embodiments of the present system may compensate for adverse influences in the main magnetic field of a main magnet using passive shimming methods. These passive shimming methods rely upon shims (e.g., passive shims) which may be formed from a shim material such as shim iron (or other ferromagnetic material) and may be placed at one or more desired locations relative to the main magnet of a corresponding MRI-LINAC system. Shim rails may span a portion of a length of a bore of a main magnet and may have shims coupled thereto at predetermined locations. Thus, these predetermined shim locations on the shim rails may be populated with shims while other shim locations are not populated with shims. A decision whether to populate a shim location with a shim (e.g., made of shim iron) may be made by shimming software operating in accordance with embodiments of the present system. It is further envisioned that embodiments of the present system may further employ active shims.

FIG. 1 shows a cutaway side view of a portion of a system in accordance with embodiments of the present system illustratively shown as an MR-LINAC system 100 (hereinafter system 100 for the sake of clarity) including a shimming system in accordance with embodiments of the present system. As discussed above, while the embodiment discussed is related to an MR-LINAC system, this illustrative discussion should be understood to include a discussion related to other radiation sources that may be suitably applied.

The system 100 may include a controller 110, a memory, a display, a body 102, a radiation source such as a linear accelerator (LINAC) 120, a shimming system 108, main magnets, gradient coil 140, and radio-frequency (RF) transducers. A movable patient support may be provided to support a patient 101 and to position the patient 101 in a desired position and/or orientation for example under the control of the controller 110.

The controller 110 may control the overall operation of the system 100 and may include one or more logic devices such as processors (e.g., microprocessors, etc.) etc. Further, the controller may receive echo information from the RF transducers and reconstruct the echo information. The reconstructed echo information may then be stored in the memory for later use and/or rendered on the display.

The gradient coil 140 may include one or more gradient coils (e.g., x-, y-, and z-gradient coils) which may produce one or more gradient fields in one or more directions under the control of the controller 110. The RF transducers may transmit RF pulses within the cavity and/or receive echo information therefrom under the control of the controller 110. For example, the RF transducers may be controlled to transmit RF pulses at the test patient 101 and/or to receive echo information therefrom.

One or more main magnets may include a bore and may be configured to generate a substantially homogenous main magnetic field within the cavity 106. The one or more main magnets may be formed from a superconducting material.

The body 102 may include the cavity 106 situated between opposed ends 105 and which may be configured to receive the patient 101 such that at least a portion of the patient 101 may be situated within a scanning volume such as a volume-of-interest (VOI) 103. One or more openings 104 may be situated at each of the respective opposed ends 105. The cavity 106 may have an exclusion zone (Ez) having opposed ends 109, and which is situated between non-exclusion zones (Nz), each of which is situated between an opposed end 109 of the Ez and an adjacent opening 104. The cavity 106 may have an interior wall 116 and may be configured such that at least a portion thereof is situated within the bore of the one or more main magnets. However, for the sake of clarity, it will be assumed that the cavity 106 corresponds with the bore of the one or more main magnets. The body 102 may include one or more other cavities in which the main magnets may be at least partially situated. Further the body 102 may include a cooling mechanism to cool the main magnets.

The LINAC 120 may include one or more radiation guns (e.g., radiation sources such as LINAC transmitters) illustratively shown as radiation gun 120' which may transmit radiation beams 121 into, or otherwise through, the Ez. Thus, the Ez may correspond with an area through which the radiation beam 121 passes (e.g., a radiation zone (Rz)). The area (or volume) defined by the Ez may further be considered a treatment zone. The radiation beam 121 may include one or more radiation beams which may be output by the radiation source such as the LINAC and may be focused in one or more locations. The radiation source such as the LINAC may be mounted to a controllable member such as a gimbal, a gantry, etc., which may move the LINAC into a desired position (e.g., with one or more degrees of freedom). For example, in some embodiments, the controllable member may rotate the LINAC 360 degrees about the body 102. The controllable member may be controlled by a user and/or the controller 110. Accordingly, in some embodiments the controllable member may be controlled by the controller 110 to position and/or orient the LINAC 120 in a desired position relative to the body 102.

At least a portion of the shimming system 108 may be situated within the cavity 106 and may be configured to enforce uniformity (e.g., to correct inhomogeneity) of the main magnetic fields within the cavity 106. The shimming system 108 may be configured to use active and/or passive shimming methods. For example, the active shimming methods may be performed using shimming coils controlled by the controller 110 and the passive shimming methods may be performed using one or more passive shims mounted at shim locations. At least a portion of the shims, such as the passive shims, may be in a path of the radiation beam 121. The passive shims may be formed using any suitable material such as shim steel and may provide shim capacity within a path of the radiation beams 121 as will be described elsewhere. For example, in some embodiments, the passive shims may be formed from magnetic materials such as electrical steel, low-carbon steel, nickel, and/or the like.

The passive shims may include discrete shims (DSs) 112 and DSs 113, and a center shim (CS) 114 each of which may be arranged to improve homogeneity of the radiation field using a shimming method performed in accordance with embodiments of the present system. For example, the DSs 112 may be located at shim locations situated within the cavity 106 only in the Nz and may be coupled to the body 102 using any suitable method or methods such as removable rails 150 or direct coupling to the body 102. The DSs 112 may be coupled to the rails 150 using any suitable method such as bolts, screws, rivets, adhesives, friction fits, rails, etc. Similarly, the DSs 113 may be located at shim locations situated within the cavity 106 only in the Nz and may be coupled to the body 102 using any suitable method or methods such as bolts, screws, rivets, adhesives, friction fits, rails, etc. Locations of the DSs 112 and 113 may be selected by any suitable method such as a shimming method operative in accordance with embodiments of the present system. The DSs 112 and/or 113 may have various shapes and/or sizes and may include one or more layers of shim iron. For example, in some embodiments the DSs 112 and/or 113 may be formed having one or more of a square, rectangular, and circular shapes. Further, in some embodiments, the DSs 112 and/or 113 may include a plurality of layers for example of thick shim iron which are welded together. A top layer (e.g., layer furthest from an interior surface of the bore may include a counter bore which may enable additional shim capacity as the shim fastener no longer sits on top of the shim but is surrounded by the shim. The DSs 112 and/or 113 may further include washer style shims (to reduce discretization error) of various thicknesses. DSs 113 may have a shape and/or size which is similar to, or different from, the shims 112.

In accordance with embodiments of the present system, the CS 114 may be situated within the Ez such that it may provide shim capacity within a path of the radiation beam 121 to enhance uniformity (e.g., to correct inhomogeneity) of the main magnetic fields. This may enable the system 100 to meet or exceed one or more uniformity specifications such as the Beethoven™ uniformity specification, if desired. The DSs 112 may be azimuthally discrete while the CS 114 may be substantially azimuthally continuous relative to a longitudinal axis (LA) of the body 102.

The CS 114 may be formed from any suitable shimming material such as electrical or low-carbon steel or the like and may have opposed edges 131 which substantially correspond with the opposed ends 109 of the Ez so that the CS 114 spans at least a length of the Ez. When viewed from the side, the CS 114 may form an annular shape (e.g., a ring) with a uniform thickness (see, FIG. 2A) and may be formed by one or more rings (e.g., a single ring or a set of sub-rings). When the CS 114 is formed from one or more rings, these rings may be referred to as sub-rings and may for example be laminated to each other after setup. In accordance with some embodiments, the CS 114 may be formed from a passive shim iron in the form of a ring of uniform thickness. As the CS 114 may have a uniform thickness, the radiation beam 121 which may penetrate therethrough may be uniform and deliver predictable dosing regardless of angle of incidence.

Figure 6:
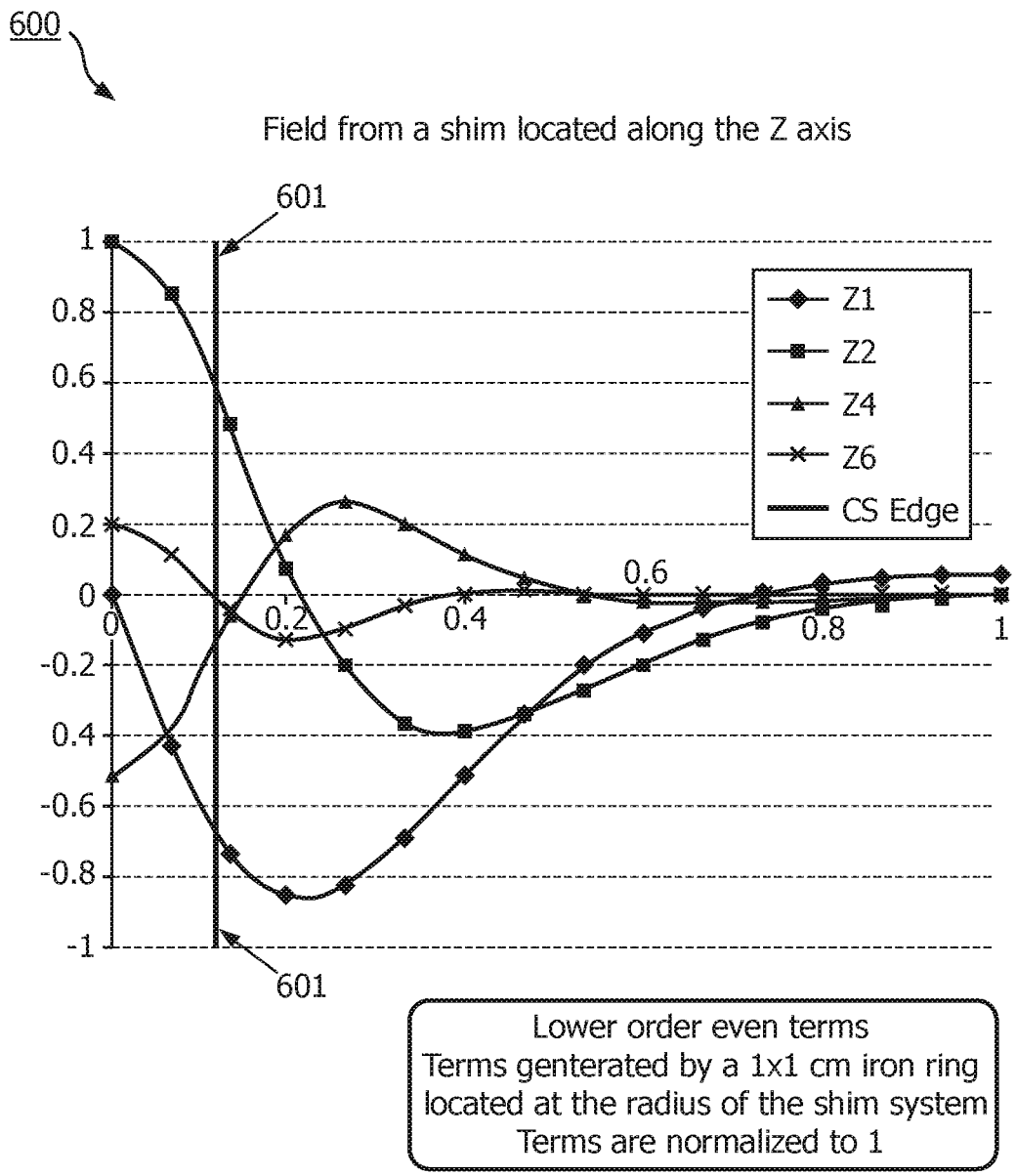
FIG. 6 is a graph 600 which shows a portion of low-order terms of an MR-LINAC system in accordance with embodiments of the present system.

Alternatively, an EZ may be created by designing the magnet with a bias (known offset) to generate terms substantially similar to that which would be produced with a CS (e.g., see FIG. 6). However, as may be readily appreciated, this strategy may be less efficient since all units may be required to have the same bias regardless of whether the magnet manufacturing tolerances required the bias or not. In accordance with embodiments of the present system, the DS would then shim out the bias applied to all magnets as well as the individual magnet tolerances.

Figure 2A:
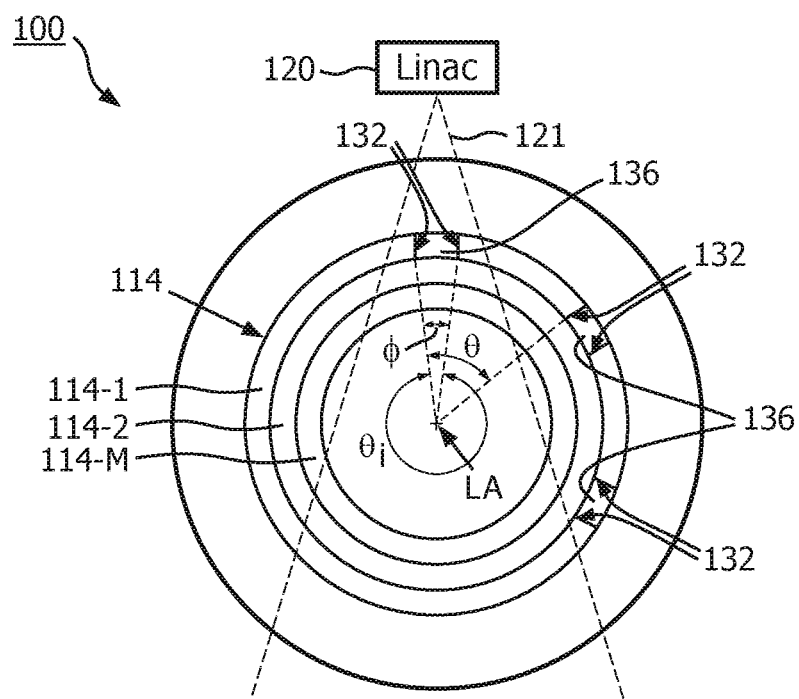
FIG. 2A shows a cross-sectional view of a portion of the MR-LINAC system taken along lines 2A-2A of FIG. 1 in accordance with embodiments of the present system.

FIG. 2A shows a cross-sectional view of a portion of MR-LINAC system 100 taken along lines 2A-2A of FIG. 1 in accordance with embodiments of the present system. The CS 114 may be formed from a plurality of annular sub-rings 114-1 through 114-M (generally 114-$x$) laminated upon each other and each being formed from a foil shim layer and having opposed edges (e.g., see 131 of FIG. 1) and ends 132. As each of the annular sub-rings 114-$x$ may be similar to each other, only a single sub-ring 114-1 will be discussed for the sake of clarity. The adjacent ends 132 may be slightly separated from each other so as to form a seam area 134 (e.g., a gap) which may be filled with a filler 136 for example after positioning. Thus, the CS 114 may be formed using a plurality of foil shim layers each forming a corresponding shim ring 114-$x$ and which may be, for example, substantially superimposed upon each other. Thus, the CS 114 may be considered to be formed from a plurality of shim layers such as shim rings 114-$x$. Each CS 114-$x$ may rotate about the longitudinal axis La (e.g., by an angle θ measured from the ends 132 of a respective CS 114-$x$) so as to substantially turn spiral, and/or rotate about the longitudinal axis by (360-Ø, where Ø is measured as an angle having a vertex at the longitudinal axis La and extending through the adjacent ends 132 of a corresponding CS 114-$x$). However, in some embodiments, one or more of the CSs 114-$x$ may turn, spiral, and/or rotate more than one turn about the longitudinal axis La. The CSs 114-$x$ may be rotationally offset from an adjacent CS 114-$x$ such as by an angle alpha (α) such that the seams 134 are staggered about a longitudinal axis (La) of the cavity 106 as shown. This may minimize worst case non-uniform attenuation and facilitate the installation of the CS 114. In an alternative configuration CA 114 may be constructed using seamless technology. The gradient coil 140 is not shown for the sake of clarity.

In accordance with some embodiments, one or more portions of the CS 114 such as the shim rings 114-$x$ may be formed from materials of varying saturation inductions to both maximize shim capacity (provided by high saturation induction materials) to correct for large magnet tolerances or environmental shielding and improved shim granularity (provided by low saturation induction materials) reducing discretization error for best shim accuracy and final system field uniformity. As may be appreciated, the use of materials of varying saturation inductions in accordance with embodiments of the present system is also useful for other MR-systems besides the MR-LINAC system described and as such, the description should be understood to include those systems that utilize those other radiation sources.

Low saturation induction materials enable very accurate solution discretization using metals of, for example, standard thicknesses and foils which may be thick enough so that they may be handled with ease (e.g., without damage) during installation of the corresponding CS or portions thereof (e.g., shim ring 114-$x$). For example, in some embodiments, the CS 114 may be completed before installation within the cavity 106. However, in yet other embodiments, the CS 114 may be completed by installing portions thereof within the cavity at separate times. For example, the shim rings 114-$x$ may be installed one at a time within the cavity so as to form the CS 114. The adjacent shim rings 114-$x$ may be attached to each other using any suitable method such as an adhesive, pressure, etc.

The gap at respective seam areas 134 may be considered a non-uniform region and may be filled with the filler 136. This filler 136 which may have a density which is substantially the same as the density of the corresponding shim ring 114-$x$ so as to keep the beam attenuation uniform. In accordance with embodiments of the present system, utilization of the filler may prevent or suppress non-uniform regions due to the gaps of a corresponding seam area 134 from causing non-uniformity within the prescribed dose. In other words, the gap filler may be configured to mitigate the impact of the center shim seams on the delivered dose. It is further envisioned that the CS 114 or portions thereof may be encapsulated in a suitable material for protection such as an epoxy, if desired.

Figure 2B:
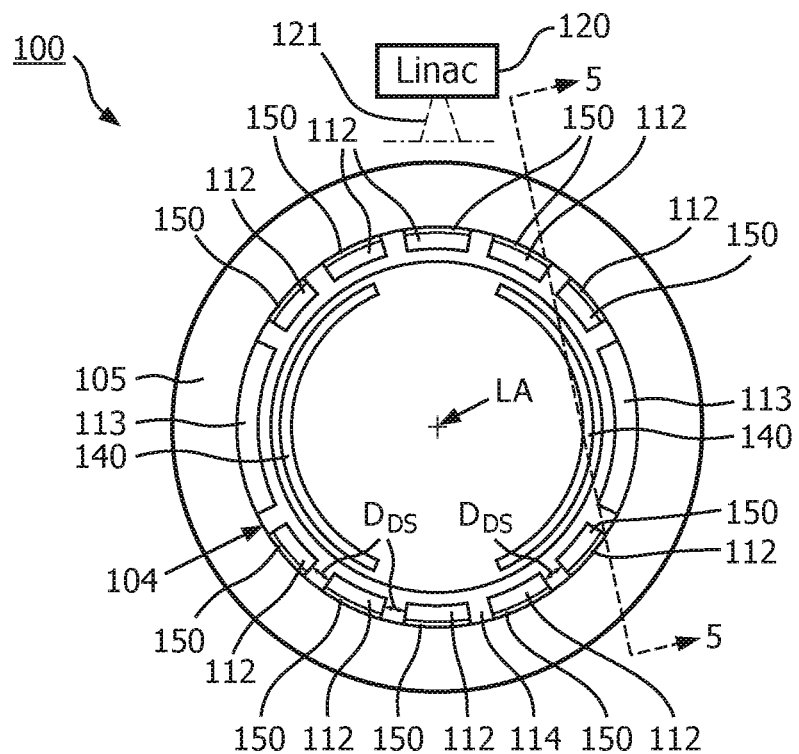
FIG. 2B shows an end view of a portion of the MR-LINAC system taken along an illustrative sectional of FIG. 1 in accordance with yet other embodiments of the present system.

FIG. 2B shows an end view of a portion of the MR-LINAC system 100 in accordance with embodiments of the present system. Adjacent DSs 112 are illustratively shown separated by gaps. As may be readily appreciated, the size of the gaps may be varied. The CS 114 may have a thickness that is greater than, equal to, or less than, a thickness of the DSs 112.

Figure 2C:
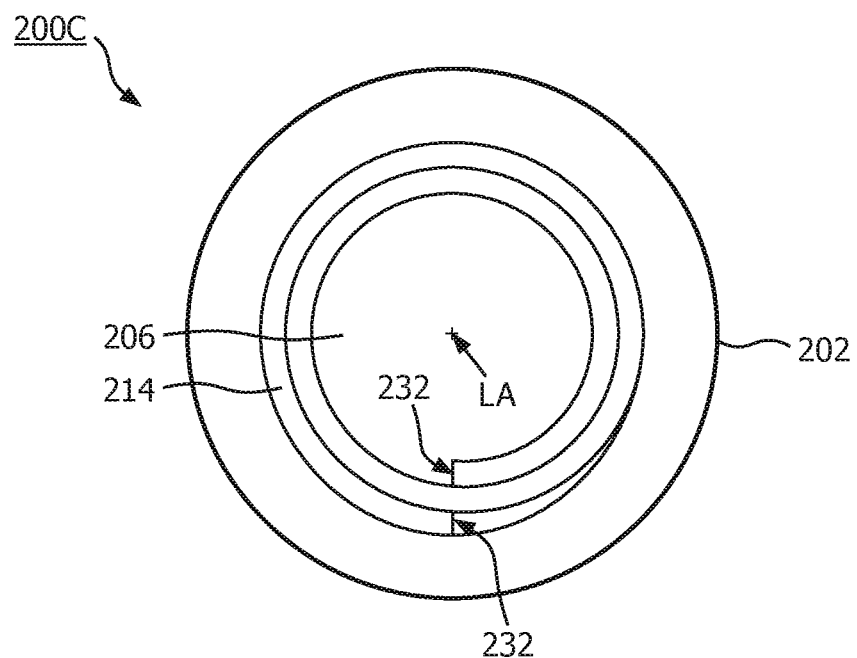
FIG. 2C shows a cross-sectional view of a portion of the MR-LINAC system including a spiral center shim in accordance with embodiments of the present system.

FIG. 2C shows a cross-sectional view of a portion of an MR-LINAC system 200C including a spiral center shim 214 in accordance with embodiments of the present system. The MR-LINAC system 200C may be similar to the system 100 shown in FIG. 2A and includes a cavity 206 in which a CS 214 is located. However, the CS 214 includes at least one turn (2 are illustratively shown) as measured from ends 232. The CS 214 is spirally wound over itself one or more times so as to form a laminated CS 214 having a desired thickness. The CS 214 may be considered continuous as it may form one or more turns. By reducing or entirely eliminating the seam areas, the CS 214 may minimize non-uniform attenuation from non-uniform regions at the seam areas (e.g., such as the seam areas 134 of the CS 114 shown in FIG. 2A). In some embodiments, the CS 214 may include any number of turns (e.g., 3, 4, 5, 6, etc.). The adjacent layers of the CS 114 may be attached to each other using any suitable method such as an adhesive, pressure, etc.

Figure 2D:
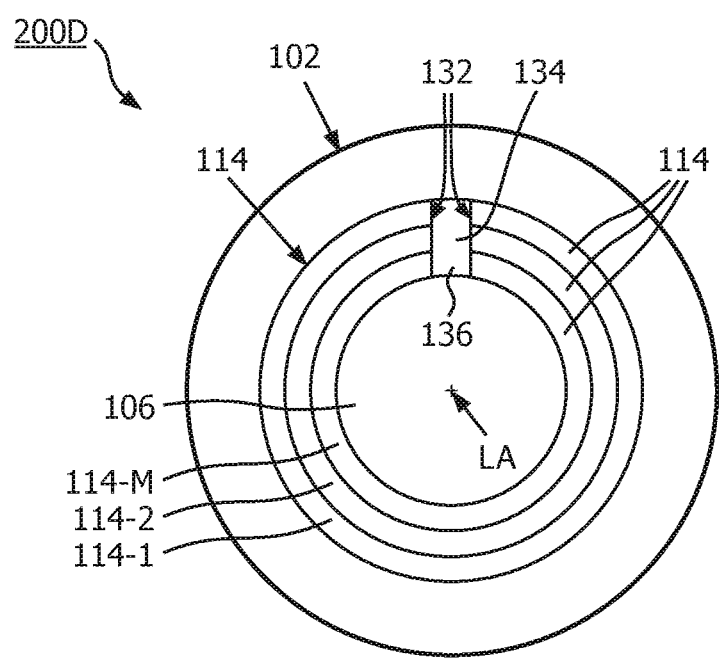
FIG. 2D shows a cross-sectional view of a portion of the MR-LINAC system taken along lines 2A-2A of FIG. 1 in accordance with embodiments of the present system.

FIG. 2D shows a cross-sectional view of a portion of the MR-LINAC system 100 illustratively including a CS of multiple layers with apposed edges with gaps of each layer aligned taken along lines 2A-2A of FIG. 1 in accordance with embodiments of the present system. This embodiment is similar to the embodiment shown in FIG. 2A. However, rather than staggering the seam areas 134 of the shim rings 114-x s shown in FIG. 2A, the gaps 134 may aligned with each other such that they may be coincident with each other (e.g., one or more, such as all the staggered gaps may be aligned with each other). Further, the shim rings 114-x may be oriented such that the non-uniform region of the gaps 134 may avoid the radiation zones and thus, penetration by the radiation beam 121. A filler may be provided to fill the gaps 134 as will be discussed herein. For example, in some embodiments the gaps 134 may be situated within an area which is not penetrated by the radiation beam 121 during use.

Figure 3:
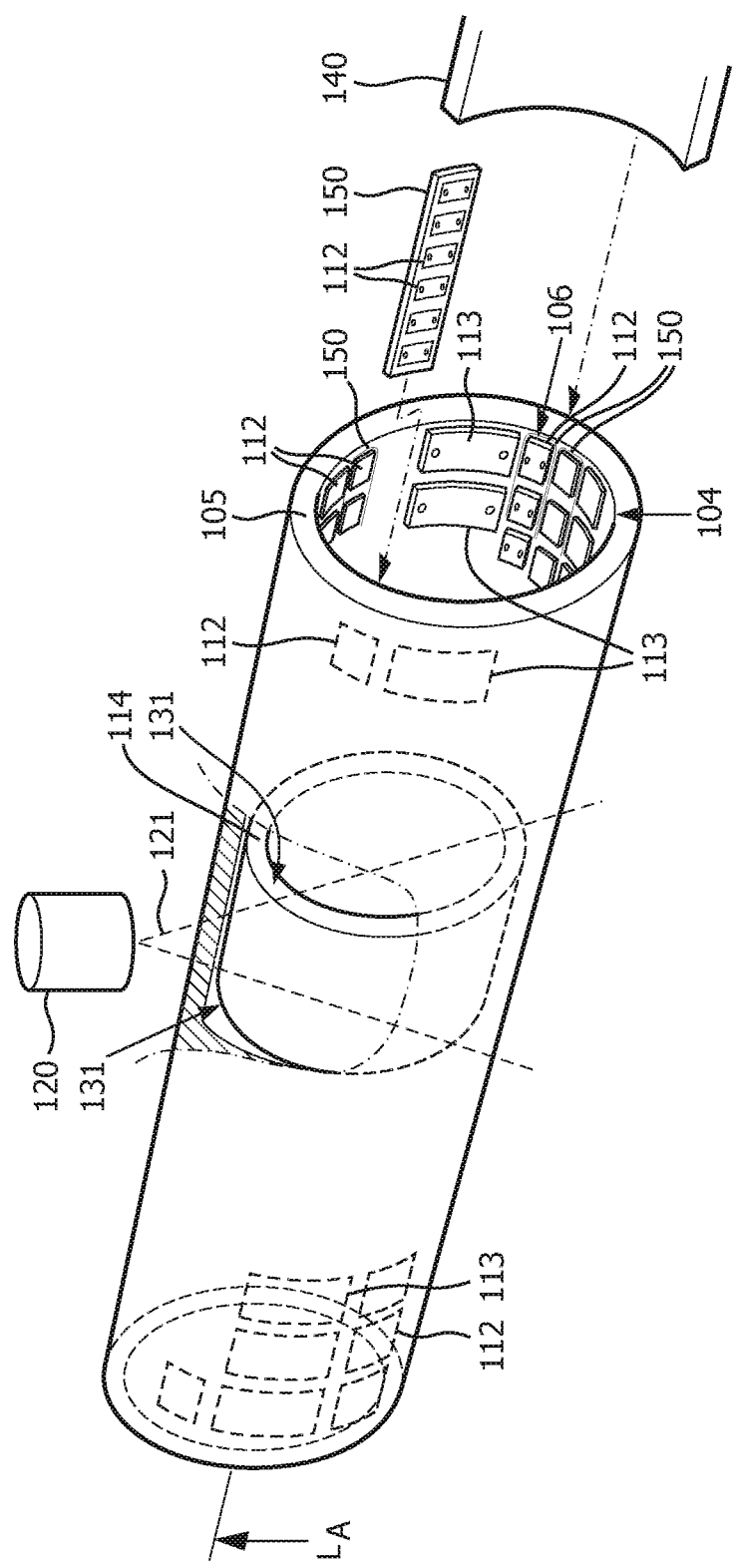
FIG. 3 shows a partially cutaway, exploded, perspective view of a portion of the MR-LINAC system in accordance with embodiments of the present system.

FIG. 3 shows a partially cutaway, exploded, perspective view of a portion of the system 100 in accordance with embodiments of the present system. A plurality of The DSs 112 may be mounted upon, or otherwise coupled to, the bore 106 of the magnet or a corresponding rail 150 of one or more rails 150. The rails 150 may slidably engage receiving rails 151 which may be coupled to the body 102. A locking system as will be described elsewhere may lock the rails 151 in a desired position. For the sake of clarity, it will be assumed that the system 100 may be substantially symmetric about one or more axes although this is not required. Accordingly, a rear view is not shown.

Figure 4:
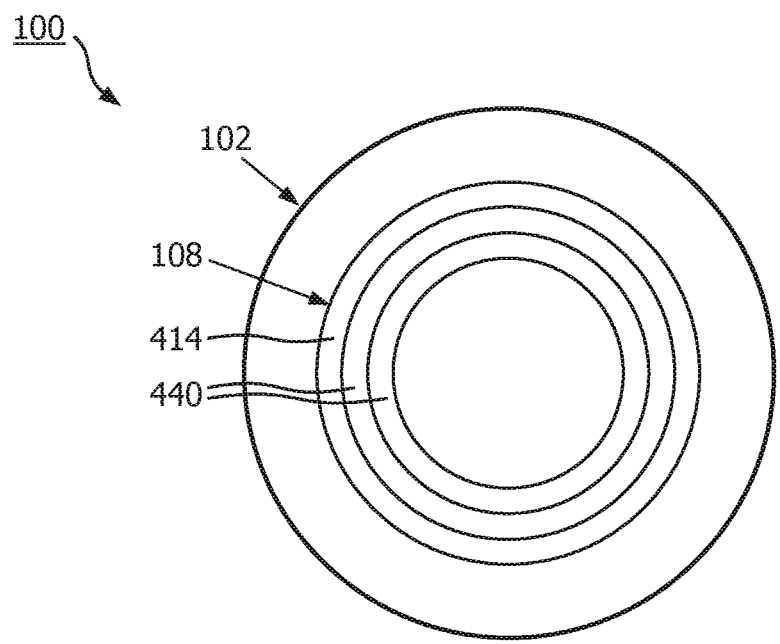
FIG. 4 shows a cross-sectional view of a portion of the MR-LINAC system taken along lines 2A-2A of FIG. 1 in accordance with embodiments of the present system.

FIG. 4 shows a cross-sectional view of a portion of the MR-LINAC system 100 taken along lines 2A-2A of FIG. 1 in accordance with embodiments of the present system. This embodiment is similar to the embodiment shown in FIG. 2A and includes a CS 414 which is similar to the CS 114. However, the CS 414 may include, one or more inner layers 440 (e.g., "inner layers") that may match the shim iron radiation absorption of the CS 414. The one or more inner layers 440 may be coupled to CS 414 using any suitable method (e.g., adhesives, epoxies, etc). Further, when the CS 414 is formed of multiple layers, these layers may be coupled (e.g., laminated) to each other using any suitable method such as adhesives, etc. The one or more inner layers 440 may be formed from any suitable material, such as a non-magnetic material and may be configured to match the shim iron radiation absorption of the center shim CS 414 so as to maintain uniform attenuation from system to system. A constant radiation absorption between MR-LINAC systems is maintained by use of non-magnetic center shim layers in combination with magnetic center shim layers to produce a fixed unit of radiation absorption. In this way, MR-LINAC systems may be produced that have substantially the same beam attenuation while reducing the magnitude of LINAC beam calibration required.

Several methods to attach and/or restrain portions of the shim system will now be discussed. According to embodiments of the present system, a center ring restraint (CRR) may be provided to hold the CS, or portions thereof, in a desired position relative to a desired portion of the MR-LINAC system such as a body or portions thereof such as a rail or a cavity of the body. The CRR may include any suitable method such as adhesives, pins, screws, biasing members (e.g., snap rings), bolts, rivets, etc. For example, in some embodiments, the CRR may include an adhesive which may be robust against radiation which may be generated by an MR-LINAC system operating in accordance with embodiments of the present system. The adhesive may include a silicone adhesive or the like which may adhere adjacent surfaces together such as a surface of a shim and the body. For example, the adhesive may be situated between the CS 114 and a surface of the body 102 such as a surface of an interior wall 116 of the cavity 106 so as to couple the CS 114 to the body 102. Thus, the CRR may position the CS 114 in a desired position within at least a portion of the Ez.

When the CRR includes mounting lugs or rings, it may be desirable to position the mounting lugs or rings outside of the Ez in an adjacent area of the Nz. For example, in an embodiment wherein the CRR includes elements that are not substantially uniform, the elements may reside outside of the EZ. Accordingly, one or more of the opposed edges of the CS may extend into the Nz so as to accommodate the mounting lugs or rings which may pass through openings in the CS. Thus, when using mounting lugs or rings to couple the CS to the body, the CS may be longer (as measured between the opposed edges) (e.g., to accommodate the mounting method such as the lug or rings) than when using adhesives. Thus, a benefit of using adhesives to couple the CS to the body is that the CS may have a shorter axial length than may be required when using other mounting methods such as lugs or rings as a CRR. It is further envisioned that any suitable attachment method or combinations of methods may be used to position the CS within the cavity of the body of the MR-LINAC system such as friction fits, screws, pins, rivets, lugs, biasing members, flanges, etc. In accordance with further embodiments of the present system, the CRR may include a non-magnetic biasing member such as a snap-ring or the like which may locate the CS in a desired position within the cavity of the body. During installation, the snap-ring may be compressed and then released to apply pressure to hold the CS against an interior wall of the cavity. It is further envisioned that the CS may be encapsulated in whole or in part using any suitable encapsulation material such as an epoxy or the like, if desired. The use of an encapsulation method such as an epoxy may offer increased protection to the CS against damage.

Figure 5:
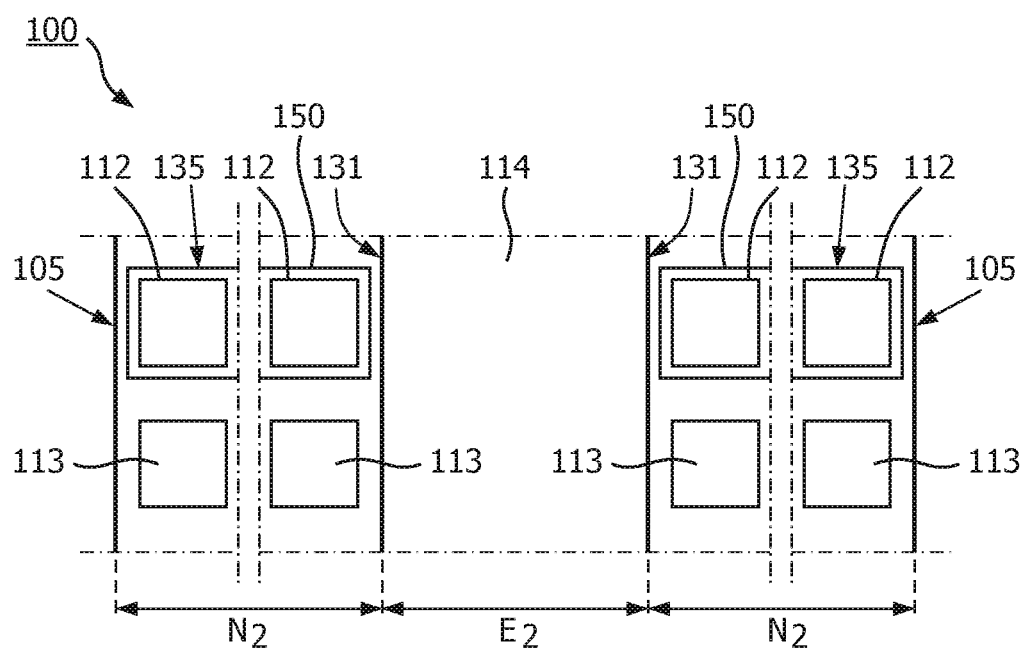
FIG. 5 shows a partial cutaway side view of a portion of the system 100 taken along lines 5-5 of FIG. 2B in accordance with embodiments of the present system.

FIG. 5 shows a partial cutaway side view of a portion of the system 100 taken along lines 5-5 of FIG. 2B in accordance with embodiments of the present system. The gradient coil 140 is not shown for the sake of clarity.

The DSs 112 and/or 113, and/or the CS 114 may be configured to receive the desired attachment method. For example, if screws or lugs are used to mount one or more of the DSs 112 to a corresponding rail 150, then these DSs 112 may include, for example, an opening configured to receive the screws or lugs for mounting. An Ez may correspond at least in part with radiation/treatment zones.

With regard to the length of the CS 114, the opposed edges 131 of the CS 114 and may extend along a longitudinal axis LA of the cavity 106 such that it at least extends up to, or axially beyond, adjacent opposed ends of the Ez. Portions of the CS 114 situated between the ends of the Ez and within an adjacent opposed edge 131 may include a mounting area which may be configured to receive the desired mounting method. For example, one or more of the mounting areas may include an opening (e.g., punched or otherwise cut out of the CS114) to receive bolts, screws, lugs or other mounting member(s) which may be coupled to the body 102 to position the CS 114 in a desired location relative to the body 102. However, in yet other embodiments, it is envisioned that that one or more of the opposed edges 131 may be welded to the body 102 or portions thereof. Although the opposed edges 131 of the CS 114 may extend into the NZ, the DSs 112 and/or the DSs 113 cannot extend into the Ez. In some embodiments, one or more of the opposed edges 131 of the CS 114 may extend up to or beyond the opposed ends of the Ez depending upon a type of mounting method used. For example, if adhesives or welding is used as a method to mount the CS 114 to the body 102, then the CS 114 may have opposed edges 131 which may extend up to or slightly past an adjacent one of the opposed ends of the Ez. Accordingly, the mounting areas may be almost nonexistent or very small. However, if studs or bolts are used as a method to mount the CS 114 to the body 102, then the CS 114 may have opposed edges 131 which may extend past up to an adjacent one of the opposed end of the Ez so as to form a larger mounting area which may be configured to receive the desired mounting method (e.g., openings to receive studs, etc.), DSs 112 and 113 may be different from each other. For example, the DSs 112 may be of a first type (e.g., with regard to material, shape, size, layers, mounting methods, etc.) while the DSs 113 may be of a different type A plurality of shims such as the shims of the first type (e.g., DSs 112) may be coupled to a corresponding rail 150 and may form a shim rail block assembly 135. Each rail 150 may be configured to be coupled to the body 102 and/or detached from the body 102. Accordingly, each shim rail block assembly 135 may be slidably attached to or removed from the body 102 as a unit. For example, a shim rail block assembly 135 having a desired shim configuration may be slidably inserted into the body 102 (as shown by arrows) and locked into place using any suitable locking mechanism thereby simplifying the shimming process. Removal may be accomplished by slidably removing a corresponding shim rail block assembly 135 in the opposite direction. Thus, the one or more shim rail block assemblies 135 may function as a shim cartridge which may be inserted into, and/or removed from, the body 102 as a unit. Accordingly, a user may assembly the shim rail block assembly 135 outside of the bore 106 of the body 102 which can reduce time required for fine shimming the system 100. One or more of the shim rail block assemblies 135 may have similar or different shim configurations. The body 102 may include a shim rail receiving mechanism which may be configured to be coupled to a corresponding shim rail 150 so that the shim rail block assemblies 535 may be inserted and/or secured from an opening 104 on a corresponding end of the body 102.

One or more of the shims may be installed/adjusted on site for adjusting the shimming of the system 600. For example, to change the configuration of the DSs 112 a shim rail block assembly 135 having a desired fine shim configuration may be installed in the cavity 106 and locked in place using any suitable locking method. Thus, one or more of the shim rail block assemblies 135 may be easily removed from the body 102 so that a configuration of the DSs 112 may be changed by removing or inserting DSs 112 at desired shim locations on the rail 150 while the rail 150 is outside of the cavity 106 of the body 102 for user convenience. It is envisioned that in some embodiments the rails 150 may be preconfigured with shims (e.g., at the factory) while in others a user may change an arrangement of the shims, as desired.

Figure 8:
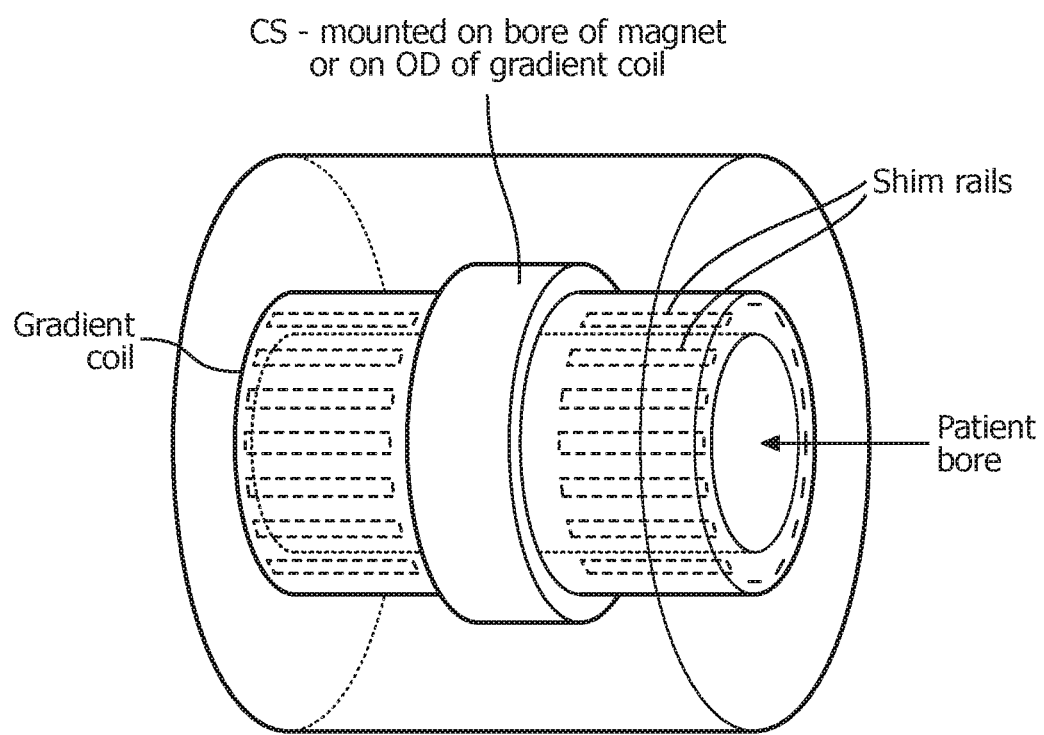
FIG. 8 shows an implementation example in which the shim rails may be mounted in the gradient coil rather than directly to the bore of the magnet in accordance with embodiments of the present system.

In accordance with embodiments of the present system, center shim rings may be installed on the bore of the main magnet and/or on an outside diameter (OD) of a gradient coil of the system as for example shown in FIG. 8. Further, it is envisioned that some systems may receive a factory pre-shim configuration that may include, for example, the mounting of the center shim in the bore of the magnet and population of the coarse shim locations. The shim rails may then be used for fine shimming onsite. It is further envisioned that in accordance with embodiments of the present system, the center ring thickness may be optimized on a per magnet bases to provide efficient shimming. Methods that depend on the same shim ring (or the same design bias thereby producing an effect substantially similar to a CS) on all magnets would likely cause the shimming on the majority of the magnets to be shimmed inefficiently in order to make the outliers usable. It is further envisioned that beam attenuation may be matched across such systems, such as all MR-LINAC systems, by applying "dummy" (non-magnetic) center shim layers as described above. These dummy shim layers may be non-magnetic shim layers which may be added to achieve a desired (e.g., matched or the same) beam-path attenuation on all such systems (e.g., all such LINAC systems) and may be added directly to an interior surface of the center shim iron or to an interior surface of the body in certain instances. For example, some magnets may require many layers of center shim iron while others may require little if any layers of center shim iron. Accordingly, if there are no layers of center shim iron installed in the main bore, then the dummy shim layer may be applied directly to an interior surface of the main bore in the center region.

Test results of an MR-LINAC system formed in accordance with embodiments of the present system will now be described with reference to FIG. 6 which is a graph 600 which shows a portion of low-order terms of an MR-LINAC system in accordance with embodiments of the present system. Graph 600 illustrates simulated terms (e.g., Z1, Z2, Z4, and Z6 (generally Zx, where x is any even integer)) determined in accordance with embodiments of the present system. The terms were simulated for a theoretical iron ring having a width (e.g., extending along the longitudinal axis (La) of the MR-LINAC system) and a thickness of 1×1 cm, respectively. For modelling, the iron ring was assumed to be located at the radius of a shim system (e.g., measured from the LA axis to the centroid of a shim location of the shim system) for the MR-LINAC in accordance with embodiments of the present system. Portions of the terms Zx which lie to the left of line 601 (e.g., the edge of the CS) would be difficult if not impossible to attain using conventional shimming methods. However, the portions of terms Zx were obtained in an MR-LINAC system using shimming methods in accordance with embodiments of the present system. Thus, shimming methods in accordance with embodiments of present system such as shown in FIG. 1 which use a CS 114 situated within an exclusion zone of an MR-LINAC system provides portions of terms Zx that would not be attainable when using conventional shimming methods if discrete shims are excluded from the beam path. Further, other systems including MR-LINAC systems including arrangements of shims in accordance with embodiments of the present system may enable systems configured in accordance with embodiments of the present system to meet world class uniformity specifications such as the Philips Ingenia specification. As made clear, the embodiments of the present system may be suitably applied with radiation delivery systems other than the LINAC radiation delivery system illustratively discussed herein. As such, the claims should be understood to include such other radiation delivery systems that for example may provide the same or similar functionality to the system.

Figure 7:
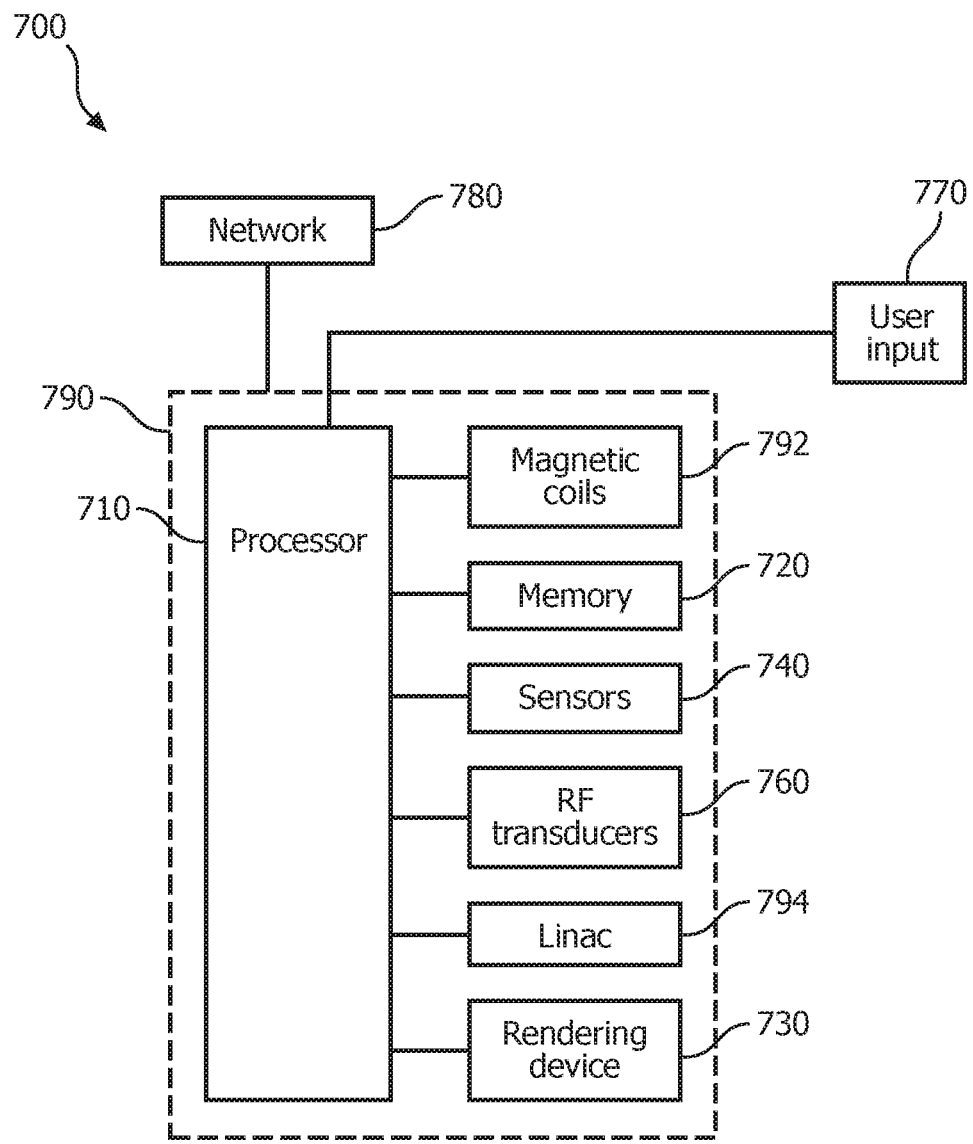
FIG. 7 shows a portion of a system 700 in accordance with embodiments of the present system.

FIG. 7 shows a portion of a system 700 in accordance with embodiments of the present system. For example, a portion of the present system may include a processor 710 (e.g., a controller) operationally coupled to a memory 720, a rendering device such as a display 730, sensors 740, RF transducers 760, magnetic coils 792, a linear accelerator (LINAC) 794, and a user input device 770. The memory 720 may be any type of device for storing application data as well as other data related to the described operation. The application data and other data are received by the processor 710 for configuring (e.g., programming) the processor inside 710 to perform operation acts in accordance with the present system. The processor 710 so configured becomes a special purpose machine particularly suited for performing in accordance with embodiments of the present system.

The operation acts may include configuring an MRI system by, for example, controlling optional support actuators, the magnetic coils 792, and/or the RF transducers 760. The support actuators may control a physical location (e.g., in x, y, and z axes) of a patient, if desired. The LINAC may be controlled by the processor 710 to output a beam with a desired shape, power, etc. The magnetic coils 792 may include main magnetic coils, gradient coils (e.g., x-, y-, and z-gradient coils), optional shimming coils, and may be controlled to emit a main magnetic field and/or gradient fields in a desired direction and/or strength. The controller may control one or more power supplies to provide power to the magnetic coils 792 so that a desired magnetic field is emitted at a desired time. The RF transducers 760 may be controlled to transmit RF pulses at the patient and/or to receive echo information therefrom. One or more of the magnetic coils may operate to receive signals such as the (MR) echo information and transform them (e.g., using one or more reconstruction techniques of embodiments of the present system) into content which may include image information (e.g., still or video images (e.g., video information)), data, and/or graphs that can be rendered on, for example, a user interface (UI) of the present system such as on the display 730, etc. Further, the content may then be stored in a memory of the system such as the memory 720 for later use. Thus, operation acts may include requesting, providing, and/or rendering of content such as, for example, reconstructed image information obtained from the echo information. The processor 710 may render the content such as image information on a UI of the system such as a display of the system.

The processor 710 may further control operation of a LINAC so as to control beam power, focus, intensity, etc. The processor 710 may further receive information related to location of one or more radiation guns of the LINAC and process this information to determine the location of the corresponding one or more radiation guns. The user input 770 may include a keyboard, a mouse, a trackball, or other device, such as a touch-sensitive display, which may be stand alone or be a part of a system, such as part of a personal computer, a personal digital assistant (PDA), a mobile phone (e.g., a smart phone), a monitor, a smart- or dumb-terminal or other device for communicating with the processor 710 via any operable link. The user input device 770 may be operable for interacting with the processor 710 including enabling interaction within a UI as described herein. Clearly the processor 710, the memory 720, display 730, and/or user input device 770 may all or partly be a portion of a computer system or other device such as a MR-LINAC system.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 720 or other memory coupled to the processor 710.

The program and/or program portions contained in the memory 720 may configure the processor 710 to implement the methods, operational acts, and functions disclosed herein. The memories may be distributed, for example between the clients and/or servers, or local, and the processor 710, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 710. With this definition, information accessible through a network is still within the memory, for instance, because the processor 710 may retrieve the information from the network for operation in accordance with the present system.

Embodiments of the present system may provide fast imaging methods to acquire and reconstruct images. Suitable applications may include imaging systems such as magnetic resonance imaging (MRI) systems which may include a LINAC to output radiation beams (e.g. which may be focused and/or directed to a desired location) and the like so as to form an MR-LINAC system. Embodiments of the present system may provide a homogeneous (or substantially homogeneous) main magnetic field in a volume of interest (VOI) which may be beneficial for providing MR-guided radiation therapy in a treatment or radiation zone while meeting or exceeding competitive uniformity specifications, such as the Ingenia™ uniformity specification. Further, embodiments of the present system may provide a homogeneous (or substantially homogeneous) main magnetic field without shims of a shim system interfering with the predictability of a radiation dose (e.g., from a LINAC) delivered to a patient situated with a cavity of the body of the system.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention. Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

The invention claimed is:

1. A magnetic resonance apparatus, comprising:
a body portion comprising a cavity having opposed ends and at least one opening situated at one of the opposed ends, the cavity defining a longitudinal axis extending between the first and second ends, an annular zone disposed between the first and second ends and around the cavity and configured to pass a radiation beam;
at least one main magnet for generating a main magnetic field comprising a substantially homogenous magnetic field within the cavity;
a radiation source for emitting at least one radiation beam through the cavity; and
a shim system comprising an annular cylindrical shim around the cavity and extending between opposed edges and which substantially encircles and extends along the longitudinal axis of the body portion,
wherein at least a portion of the annular cylindrical shim is disposed in a path of the radiation beam.

2. The apparatus of claim 1, wherein the shim system further comprises a plurality of discrete shims situated between an edge of the opposed edges of the cylindrical shim and an adjacent one of the opposed ends of the cavity.

3. The apparatus of claim 2, wherein the cylindrical shim comprises a plurality of shim layers laminated upon each other.

4. The apparatus of claim 2, wherein the shim system further comprises one or more rails each configured to be coupled to a plurality of the discrete shims.

5. The apparatus of claim 1, wherein the cylindrical shim comprises a spirally wound sheet having N turns, wherein N is an integer greater than 2.

6. A magnetic resonance apparatus, comprising:
a body portion comprising a cavity having opposed ends and at least one opening situated at one of the opposed ends, the cavity defining a longitudinal axis extending between the first and second ends, an annular zone disposed between the first and second ends and around the cavity and configured to pass a radiation beam;
at least one main magnet for generating a main magnetic field comprising a substantially homogenous magnetic field within the cavity;
a radiation source for emitting at least one radiation beam through the cavity; and
a shim system comprising an annular cylindrical shim which substantially encircles and extends along the longitudinal axis of the body portion,
wherein the annular cylindrical shim comprises a plurality of sub-shims laminated radially upon each other,
wherein at least one of the sub-shims has opposed edges situated apart from each other so as to define a gap, and
wherein the gap extends parallel to the longitudinal axis.

7. The apparatus of claim 6, further comprising a filler situated in the gap.

8. The apparatus of claim 6, wherein each of the plurality of sub-shims has corresponding opposed edge situated apart from each other so as to define a corresponding gap, and wherein the gap of each of the sub-shims is rotationally offset from the gap of the other sub-shims so as to be staggered.

9. The apparatus of claim 6, wherein each of the plurality of sub-shims has corresponding opposed edge situated apart from each other so as to define a corresponding gap, and wherein the gap of at least one sub-shim is rotationally offset from the gap of another sub-shim so as to be staggered.

10. The apparatus of claim 6, wherein each of the plurality of sub-shims has corresponding opposed edge situated apart from each other so as to define a corresponding gap, and wherein the gap of each sub-shim is aligned with the gaps of the other sub-shims.

11. The apparatus of claim 6, wherein at least a portion of the annular cylindrical shim is disposed in a path of the radiation beam.

12. The apparatus of claim 6, wherein the annular cylindrical shim is a passive shim comprising a magnetic material.

13. The apparatus of claim 6, wherein the shim system further comprises a plurality of discrete shims situated between an edge of the opposed edges of the cylindrical shim and an adjacent one of the opposed ends of the cavity.

14. The apparatus of claim 13, wherein the shim system further comprises one or more rails each configured to be coupled to a plurality of the discrete shims.

15. The apparatus of claim 1, wherein the annular cylindrical shim has opposed edges situated apart from each other so as to define a gap, wherein the gap extends parallel to the longitudinal axis, and wherein the apparatus further comprises a filler situated in the gap.

16. A magnetic resonance apparatus, comprising:
a body portion comprising a cavity having opposed ends and at least one opening situated at one of the opposed ends, the cavity defining a longitudinal axis extending between the first and second ends, an annular zone disposed between the first and second ends and around the cavity and configured to pass a radiation beam;
at least one main magnet for generating a main magnetic field comprising a substantially homogenous magnetic field within the cavity;
a radiation source for emitting at least one radiation beam through the cavity; and
a shim system comprising a passive annular cylindrical shim around the cavity and extending between opposed edges and which substantially encircles and extends along the longitudinal axis of the body portion.

17. The magnetic resonance apparatus of claim 16, wherein at least a portion of the passive annular cylindrical shim is disposed in a path of the radiation beam.

18. The magnetic resonance apparatus of claim 16, wherein the annular cylindrical shim has opposed edges situated apart from each other so as to define a gap, wherein the gap extends parallel to the longitudinal axis, and wherein the apparatus further comprises a filler situated in the gap.

19. The magnetic resonance apparatus of claim 16, wherein the cylindrical shim comprises a spirally wound sheet having N turns, wherein N is an integer greater than 2.

20. The magnetic resonance apparatus of claim 16, wherein the shim system further comprises a plurality of discrete shims situated between an edge of the opposed edges of the cylindrical shim and an adjacent one of the opposed ends of the cavity.

* * * * *